(12) United States Patent
Klemm et al.

(10) Patent No.: US 12,743,113 B2
(45) **Date of Patent: *Sep. 22, 2026**

(54) METHOD FOR CONTROLLING OVERPRESSURE IN ORAL-CARE IMPLEMENT

(71) Applicant: Braun GmbH, Kronberg (DE)

(72) Inventors: Torsten Klemm, Eschborn (DE); Ferdinand Hermann, Koenigstein (DE); Bettina Rowlands, Bad Homburg (DE); Isabel Cecilia Martinez, Kronberg (DE); Lutz Lisseck, Schwalbach am Taunus (DE); Norbert Schaefer, Frankfurt am Main (DE); Karen Lynn Claire-Zimmet, Kronberg (DE)

(73) Assignee: Braun GmbH, Kronberg (DE)

( * ) Notice: Subject to any disclaimer, the term of this patent is extended or adjusted under 35 U.S.C. 154(b) by 657 days.

This patent is subject to a terminal disclaimer.

(21) Appl. No.: 18/133,363

(22) Filed: Apr. 11, 2023

(65) Prior Publication Data

US 2024/0345607 A1 Oct. 17, 2024

(51) Int. Cl.
*G05D 15/01* (2006.01)
*A61C 17/22* (2006.01)
(Continued)

(52) U.S. Cl.
CPC ........... *G05D 15/01* (2013.01); *A61C 17/221* (2013.01); *G05B 19/416* (2013.01); *G16H 40/63* (2018.01);
(Continued)

(58) Field of Classification Search
CPC ...... G05D 15/01; A61C 17/221; A61C 17/26; A61C 17/34; G05B 19/416;
(Continued)

(56) References Cited

U.S. PATENT DOCUMENTS 5,784,742 A * 7/1998 Giuliani ............... A61C 17/221 340/665
9,687,329 B2 6/2017 Lee
(Continued)

OTHER PUBLICATIONS

PCT Search Report and Written Opinion for PCT/IB2024/053557 dated Jul. 15, 2024, 16 Pages.
(Continued)

*Primary Examiner* — Mong-Shune Chung
(74) *Attorney, Agent, or Firm* — Jay A. Krebs

(57) ABSTRACT

A method for controlling overpressure in an electric oral-care implement having a treatment head with at least one functional element driven by a motor. The method includes detecting a stimulus to energize the motor, setting a baseline current, and repeatedly execute an overpressure-detection control loop, said loop including measuring the motor's instantaneous current draw, adding an increment value to the baseline current or subtracting a decrement value from the baseline current thereby generating a dynamically adjusted baseline current, determining whether a difference between the instantaneous current draw and the dynamically adjusted baseline current exceeds a threshold thereby detecting an occurrence of overpressure, and performing a corrective action in response to the detected occurrence of overpressure.

28 Claims, 2 Drawing Sheets

(51) Int. Cl.
*G05B 19/416* (2006.01)
*G16H 40/63* (2018.01)

(52) U.S. Cl.
CPC .............. *G05B 2219/37399* (2013.01); *G05B 2219/45167* (2013.01)

(58) Field of Classification Search
CPC ........... G05B 2219/37399; G05B 2219/45167; G16H 40/63; A46B 13/02; A46B 2200/1066; A46B 15/0012
See application file for complete search history.

(56) References Cited

U.S. PATENT DOCUMENTS

| | | | | |
|---|---|---|---|---|
| 10,561,480 | B2 | 2/2020 | Luettgen et al. | |
| 11,413,125 | B2 | 8/2022 | Follows | |
| 2013/0091642 | A1* | 4/2013 | Dykes | A61B 5/4552 15/22.1 |
| 2014/0310900 | A1 | 10/2014 | Curry | |
| 2016/0045081 | A1* | 2/2016 | Kern | A46B 13/008 15/22.4 |
| 2017/0319311 | A1* | 11/2017 | Luettgen | A46B 15/0012 |
| 2019/0090999 | A1* | 3/2019 | Vetter | A46B 15/0012 |
| 2020/0390228 | A1 | 12/2020 | Farrell | |
| 2021/0112965 | A1* | 4/2021 | Jeanne | G16H 50/30 |
| 2022/0331079 | A1* | 10/2022 | Ogunsina | A46B 15/0006 |

OTHER PUBLICATIONS

All Office Actions: U.S. Appl. No. 18/133,359, filed Apr. 11, 2023.
Unpublished U.S. Appl. No. 18/133,359, filed Apr. 11, 2023, to Torsten Klemm et al.

* cited by examiner 112
113
160
110
10
121
111
120
126
123
125
122

130
110
170
140
10
151
120
150
126
125
124
152

METHOD FOR CONTROLLING OVERPRESSURE IN ORAL-CARE IMPLEMENT

FIELD OF THE INVENTION

The present disclosure is directed to electric oral-care implements, such as an electric toothbrush, having a pressure-control system, and methods for controlling pressure in such implements.

BACKGROUND OF THE INVENTION

Personal care and grooming have become an important part of today's lifestyle of many consumers. Modern personal-care products, such as, e.g., oral-care implements, rely on electric power to deliver good-quality results expected by consumers. Such oral-care electric appliances possess technologically advanced features—and increased use of electric toothbrushes reflects a growing awareness among consumers of the advantages delivered thereby, e.g., convenience, efficacy, and health benefits. As compared to conventional manual toothbrushes, an electric toothbrush can deliver superior brushing results.

An electric toothbrush typically comprises a toothbrush handle, having a battery and an electric motor housed therein, and a replaceable toothbrush head, removably attached to the toothbrush handle. The toothbrush head includes a movable functional element, e.g., a bristle holder, having cleaning elements, e.g., tufts of bristles, located at a free end of the toothbrush head. The motor in the toothbrush handle controls movement of the functional element, causing cleaning elements to move. Such movement may include, e.g., movement up and down, side to side, movement in a pattern of a circular movement, i.e., oscillating, rotating, and the like. In some electric toothbrushes, the bristles heads are designed for vibration.

While electric toothbrushes can provide superior benefits, a common potential problem in electric toothbrushes is an excessive pressure, or overpressure. Overpressure commonly occurs when a user operating an electric toothbrush applies a high level of pressure (typically applied with a non-electric toothbrush) while brushing. Such an excessive pressure may result in inferior cleaning results, as an electric brush is not designed to be used with a high pressure during brushing. Also, if a user applies excessive pressure over a substantial period of time, a damage to the user's gums may occur. Therefore, there is a desire to monitor—and prevent—the application of the excessive pressure to the toothbrush bristles by a user, so that the force applied by the user during brushing remains below an undesirable and potentially harmful level.

Various pressure-sensing devices used in electric (and manual) toothbrushes to determine and/or limit the pressure applied to the bristles during brushing are known. For example, as is generally understood in the art, the current draw from an electric motor in a toothbrush varies proportionally to the amount of pressure applied to the brush head. Several prior-art attempts to address the problem of overpressure in electric toothbrushes are summarized herein below.

U.S. Pat. No. 5,784,742 is directed to an electric toothbrush with an adaptive load sensor. The toothbrush includes a brush head that is vibrated by a drive assembly. The load sensor monitors the current drawn by the drive assembly to determine the mechanical load to which the toothbrush is exposed. The load sensor assembly produces an adaptive threshold signal that represents the instantaneous maximum pressure load. If the sensed load voltage exceeds the adaptive threshold signal, the load sensor assembly deenergizes the drive assembly and generates an alarm signal so as to give the user a warning that the toothbrush has been excessively loaded.

U.S. Pat. No. 9,687,329 is directed to an electric toothbrush comprising a brush head, a motor, and a controller. The controller drives the motor with a power module and senses a current of the motor that drives the motor in a pulse-activated mode when the sensed current exceeds the predetermined current threshold. The pulse-activated mode causes a pulsating bristle tuft motion, which reminds the person to release the brush pressure. The controller will then disable the motor and warn the person if the brush pressure remains.

U.S. Pat. No. 10,561,480 B2 is directed to a toothbrush that includes a control assembly that monitors a current draw by a direct-current motor and adjusts a current applied to the motor based on the current draw. The motor control may alert a user when the applied force exceeds a threshold and/or adjust the operation of the motor accordingly. The threshold may be a change of the current (e.g., current delta) from a no-load or normal-load current value. Thus, the toothbrush is tracking a delta change from an operating or no-load current draw by the motor. The initial current draw is assumed to be indicative of the no-load current draw. If the initial load is greater than an acceptable no-load condition, a default or historical no-load condition is applied to initialize the readings. To track the current draw, a sensing module tracks the mechanical load experienced on the bristles by tracking the current applied to the motor. The current drawn by the motor is proportional to the load (e.g., the force required to move the bristles), and as the load increases the current drawn by the motor also increases. If the pressure exceeds the threshold, the control assembly provides an output to the user, such as, e.g., vibration of the brush handle, activation of one or more lights, turning the motor off, producing a buzz or other audible sound, creating a stutter motion by the brush tip, and the like.

One challenge in conducting overpressure detection in an electric toothbrush is setting an appropriate threshold for the occurrence of overpressure. The current draw may naturally change depending on the particular brush head and its mechanical characteristics, including forces of friction existing among the mechanical elements thereof, as well as an extent of their wear and tear. Thus, for each brushing event, there is a need to dynamically set and adjust an overpressure threshold that would factor in various changing circumstances mentioned herein.

Accordingly, the present disclosure addresses the problem of overpressure in an electric oral-care implement, such as, e.g., an electric toothbrush. The present disclosure is directed to an electric oral-care implement having an overpressure-detection system that is configured to monitor the motor current draw to detect overpressure events and automatically perform a remedial action—and at the same time avoids inadequacies of the prior-art devices and systems. The present disclosure is also directed to a method for controlling overpressure in an electric oral-care implement.

SUMMARY OF THE DISCLOSURE

The present disclosure provides an oral-care implement comprising a pressure-control system that does not assume that an initial current draw of the motor represents a no-load condition. Instead, the pressure-control system described herein calculates a dynamically adjusted baseline current. The present disclosure further provides a method for controlling overpressure in the electric oral-care implement.

The present disclosure provides, in one aspect, an oral-care implement, such as a toothbrush, comprising a handle containing therein an electric battery in electrical communication with an electric motor having a motor shaft. The toothbrush has a motion transmitter that is operatively connected to the motor shaft. The toothbrush includes a treatment head having at least one functional element in operative communication with the motion transmitter to be driven thereby. The treatment head can be structured and configured to be attachable to and detachable from the handle, as is known in the art.

The toothbrush further includes a pressure-control system in electrical communication with the motor. The pressure-control system comprises a controller (e.g., a microcontroller) configured to detect a stimulus to energize the motor, set a baseline current, and repeatedly execute an overpressure-detection control loop to detect an occurrence of overpressure. To set the baseline current, the microcontroller can be configured to measure a current draw of the motor and to set the baseline current to the measured current draw. Alternatively, to set the baseline current, the microcontroller can be configured to set the baseline current to a predetermined value. In one embodiment that predetermined value can be from about 100 mA to about 600 mA.

The overpressure-detection control loop comprises measuring an instantaneous current draw of the motor; adding an increment value to the baseline current or subtract a decrement value from the baseline current, thereby generating a dynamically adjusted (calculated) baseline current; determining whether a difference between the instantaneous current draw and the dynamically adjusted baseline current exceeds a threshold, thereby detecting an occurrence of overpressure; and causing the oral-care implement to perform a corrective action in response to the detected occurrence of overpressure. In one embodiment, the microcontroller is configured to detect whether the occurrence of overpressure has been eliminated. The overpressure-detection control loop to detect an occurrence of overpressure can be repeatedly executed every 1-1000 milliseconds, and more specifically every 5-100 milliseconds. In one example embodiment, the overpressure-detection control loop is executed once every 10 milliseconds.

It may be beneficial to have the dynamically adjusted baseline current at a lower end of the motor current. Many electric-brush users tend to apply load continuously during brushing. Although users may reduce pressure during brushing, that typically happens only for a relatively short period of time. Therefore, the decrease of the baseline current needs to happen much faster than the baseline current's increase, as the low-load condition is significantly shorter than the high-load condition. On the other hand, as long as the load is applied, the dynamically adjusted baseline current is incrementally increased at a slower rate until the baseline current and the motor current have approximately the same value.

Tests have shown that it could be difficult to achieve high accuracy in managing overpressure if decreasing the dynamically adjusted baseline current occurs too slowly. The speed of the decrease of the dynamically adjusted baseline current can be within a range of from about 0.66 mA/sec to about 6000 mA/sec. In one example embodiment, the speed of about 200 mA/sec (or faster) of the dynamically adjusted baseline current's decrease was found to be particularly advantageous. Conversely, the speed of the increase of the dynamically adjusted baseline current can be within a range of from about 0.03 mA/sec to about 600 mA/sec. In one example embodiment, the speed of the dynamically adjusted baseline current's increase is about 10 mA/sec.

Likewise, it is believed that setting the increment value and the decrement value so that the latter is significantly larger than the former would be beneficial for the purposes of the overpressure-detection control loop. The decrement value could be at least ten times, twenty times, and even thirty times greater than the increment value. For example, the decrement value can be from about 0.66 mA to about 6 mA. In one example embodiment, the decrement value is about 2 mA. The increment value can be from about 0.03 mA to about 0.6 mA. In one example embodiment, the increment values is about 0.1 mA.

To determine whether a difference between the instantaneous current draw and the dynamically adjusted baseline current exceeds the threshold, the microcontroller can be configured to add the threshold to the dynamically adjusted baseline current. The threshold may comprise a high-load threshold indicative of a loaded state of the motor, and a low-load threshold indicative of a low-load state of the motor.

If the difference between the instantaneous current draw and the dynamically adjusted baseline current equals to or exceeds the high-load threshold, the corrective action may comprise configuring the motor to cause the at least one functional element to move with a second intensity different from the first intensity. The corrective action can be selected from the group consisting of slowing the motor, generating a light signal, generating a haptic signal, generating a sound signal, and any combination thereof.

Slowing the motor may cause a brush head, having cleaning elements thereon, move (e.g., rotate or oscillate) with a decreased frequency or amplitude. In a vibrating toothbrush, the intensity of vibration can be decreased. The microcontroller can be further configured to increase the speed of the motor back to its original speed in response to detecting that the occurrence of overpressure has been eliminated. If no overpressure is detected, the microcontroller configures the motor to cause the at least one functional element to move with a first (i.e., "normal") intensity, wherein no corrective action is performed.

To detect whether the occurrence of overpressure has been eliminated, the microcontroller can be configured to determine whether the difference between the instantaneous current draw and the dynamically adjusted baseline current is less than the low-load threshold. If the difference between the instantaneous current draw and the dynamically adjusted baseline current is less than the low-load threshold, the microcontroller configures the motor to cause the at least one functional element to move with the first intensity.

In one embodiment, the microcontroller is configured to implement a stabilization phase (or step) in response to the detection of the stimulus to energize the motor. The stabilization phase allows the motor to reach its performance equilibrium. During the stabilization phase, the microcontroller delays the measuring of the current draw and setting the baseline current. The stabilization phase may last from about 500 milliseconds to about 5000 milliseconds, and more specifically from about 1000 millisecond to about 3000 milliseconds. In one example embodiment, the stabilization phase lasts for about 2000 milliseconds. The stabilization phase also allows a user to have sufficient time to bring the toothbrush to the user's teeth and apply pressure to the toothbrush cleaning elements before the cleaning elements begin to move.

One can measure a current draw when no pressure is applied to the cleaning elements (a "no-load" condition) to set the overpressure threshold to some predetermined value above the no-load current. However, most users of electric toothbrushes naturally prefer to enable the toothbrush when the toothbrush is already in the user's mouth and pressure is applied to the cleaning elements. If a user were to enable an electric toothbrush outside of the user's mouth, the rapid movement of toothbrush's cleaning elements (whether rotational oscillation or vibration) would almost inevitably cause water and toothpaste to splatter about-a highly undesirable occurrence for toothbrush users. Thus, the conventional approaches that rely on measurement of a no-load condition are considered not reliable as they provide unsatisfactory results when implemented with electric toothbrushes.

For at least these reasons, the pressure-control system of the oral-care implement disclosed herein does not assume that an initial current draw of the motor represents a no-load condition. Instead, an algorithm implemented in the pressure-control system of the present disclosure calculates a dynamically adjusted baseline current and determines whether a difference between the instantaneous current draw and the dynamically adjusted baseline current exceeds a high-load threshold, thereby detecting an occurrence of overpressure.

According to the present disclosure, as the microcontroller does not measure the current draw during the stabilization phase, no baseline is set based on the no-load condition if the user applies pressure to the cleaning elements during the stabilization phase. Instead, the microcontroller will set the baseline under the load condition, after the expiration of the stabilization phase and while a user has already applied pressure to the cleaning elements of the toothbrush.

In another aspect, the present disclosure provides a method for controlling overpressure in an electric oral-care implement having a handle, a motor, and a treatment head with at least one functional element driven by the motor. The method comprises the steps of detecting a stimulus to energize the motor; setting a baseline current; and repeatedly execute an overpressure-detection control loop. The step of setting the baseline current can be accomplished by measuring a current draw of the motor and setting the baseline current to the measured current draw. Alternatively, setting the baseline current can be accomplished by setting the baseline current to a predetermined value, e.g., the value of from about 100 mA to about 600 mA.

In one embodiment, the step of repeatedly executing an overpressure-detection control loop is implemented every 1-1000 milliseconds, and more specifically every 5-100 milliseconds. In one example embodiment, the step of repeatedly executing an overpressure-detection control loop is implemented every 10 milliseconds. Optionally, a waiting period can be implemented between the end of one loop and the beginning of the next loop, depending on the desired frequency and duration thereof.

The overpressure-detection control loop comprises measuring an instantaneous current draw of the motor; adding an increment value to the baseline current or subtract a decrement value from the baseline current, thereby generating a dynamically adjusted baseline current; determining whether a difference between the instantaneous current draw and the dynamically adjusted baseline current exceeds a threshold, thereby detecting an occurrence of overpressure; and performing a corrective action in response to the detected occurrence of overpressure.

The step of adding an increment value to the baseline current or subtracting a decrement value from the baseline current comprises adding the increment value to the baseline current if the instantaneous current is equal to or higher than the baseline current, or subtracting the decrement value from the baseline current if the instantaneous current is lower than the baseline current. In one embodiment, the decrement value is greater than the increment value. The decrement value could be at least ten times, twenty times, and even thirty times greater than the increment value. In one example embodiment, the decrement value is about 2 mA. In one example embodiment, the increment value is about 0.1 mA.

The step of determining whether a difference between the instantaneous current draw and the dynamically adjusted baseline current exceeds the threshold comprises adding the threshold to the dynamically adjusted baseline current. The method may further include a step of determining whether the occurrence of overpressure has been eliminated.

The method may further include a stabilization step implemented in response to the detection of the stimulus to energize the motor. The stabilization step, during which the measuring a current draw of the motor to setting the baseline current is delayed, can last from about 500 milliseconds to about 5000 milliseconds, and more specifically from about 500 milliseconds to about 5000 milliseconds. In one example embodiment, the stabilization step lasts about 2000 milliseconds.

The step of causing the oral-care implement to perform a corrective action in response to the detected occurrence of overpressure comprises causing the oral-care implement to perform a corrective action selected from the group consisting of slowing the motor, generating a light signal, generating a haptic signal, generating a sound signal, and any combination thereof. In one embodiment, the step of causing the oral-care implement to perform a corrective action in response to the detected occurrence of overpressure comprises configuring the motor to cause the at least one functional element to move with a second intensity different from the first intensity. Causing the at least one functional element to move with a second intensity may include slowing the speeds of the motor's rotation. The method may further include a step of increasing the speed of the motor back to its original speed in response to detecting that the occurrence of overpressure has been eliminated.

The step of determining whether a difference between the instantaneous current draw and the dynamically adjusted baseline current exceeds a threshold may include determining whether a difference between the instantaneous current draw and the dynamically adjusted baseline current exceeds a high-load threshold that is indicative of a loaded state of the motor. Detecting whether the occurrence of overpressure has been eliminated may comprise determining whether the difference between the instantaneous current draw and the dynamically adjusted baseline current is less than a low-load threshold that is indicative of a low-load state of the motor, in which instance the motor is configured to cause the at least one functional element to move with a first intensity.

BRIEF DESCRIPTION OF THE DRAWINGS

The invention is described in more detail below with reference to various non-limiting embodiments and exemplary figures, wherein.

DETAILED DESCRIPTION

In the context of the present description, the terms “treatment force” or “treatment pressure” (or simply “force” or “pressure”) may be used herein interchangeably and means a force that is applied at the treatment head in a treatment direction. In an electric toothbrush, the treatment direction is most typically a direction that is substantially perpendicular to the longitudinal axis of the toothbrush head. Although the total applied treatment force (i.e., the force applied in more than one direction) may be higher than the treatment force applied predominantly in the treatment direction, the components of the treatment force that are acting in directions other that the treatment direction are discounted, as those force components applied at the treatment head in directions other than the treatment direction are essentially absorbed in the bearings or by elastic deformation of the oral-care implement.

Figures 1, 2:
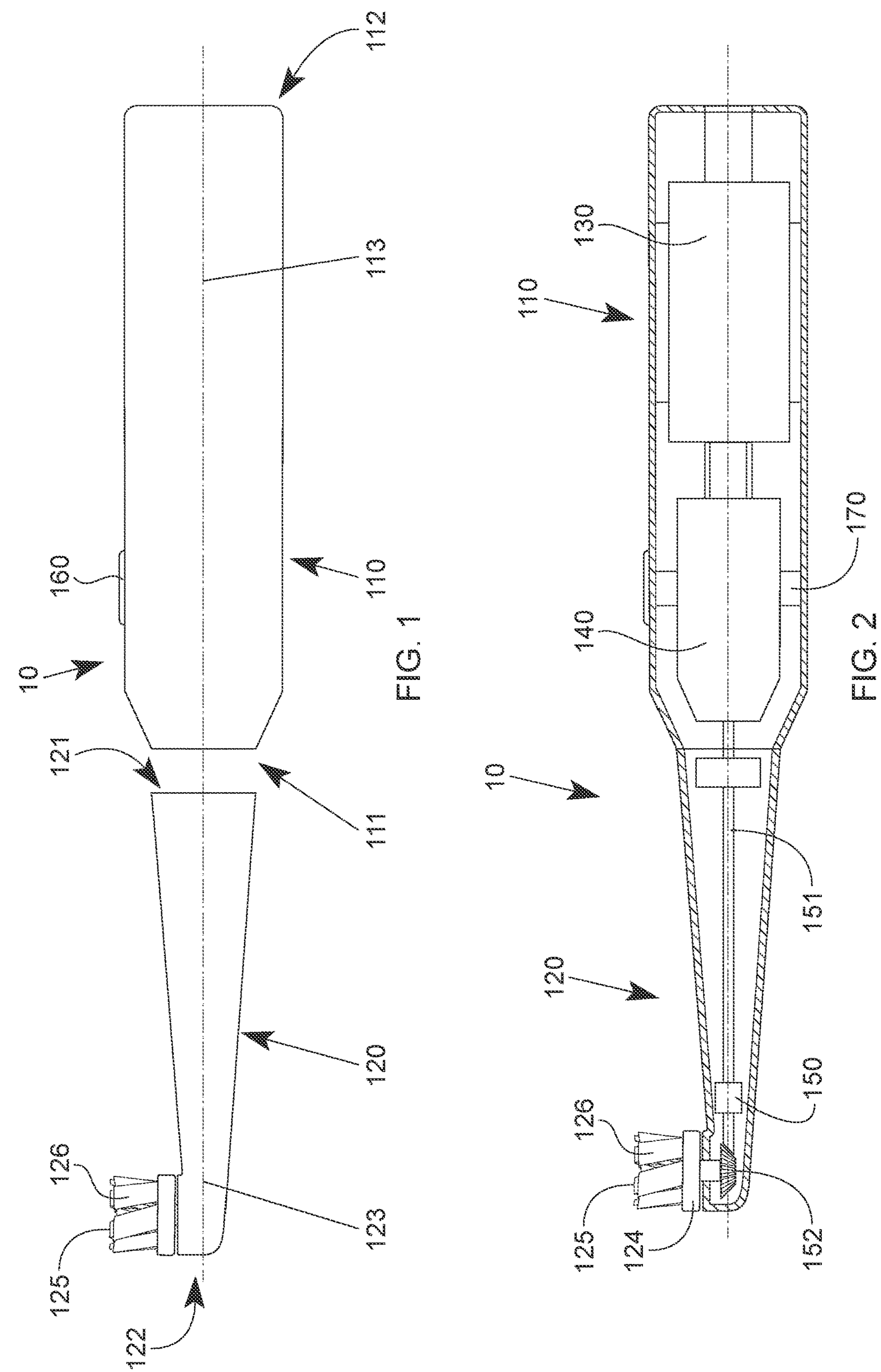
FIG. 1 is a schematic side view of an embodiment of an oral-care implement comprising an electric toothbrush.
FIG. 2 is a schematic cross-sectional view of the electric toothbrush shown in FIG. 1.

An embodiment of an oral-care implement comprising an electric toothbrush 10, according to the present disclosure, is illustrated in FIG. 1. The toothbrush 10 comprises a toothbrush handle 110 and a toothbrush head 120 that can be attached to and detached from the toothbrush handle 110. The toothbrush handle 110 has a first end 111 and a second end 112 opposite to the first end 111, and a longitudinal axis 113 extending between the first and second ends 111, 112 of the toothbrush handle 110. Likewise, the toothbrush head 120 has a first end 121 and a second end 122 opposite to the first end 121, and a longitudinal axis 123 extending between the first and second ends 121, 122 of the toothbrush head 120. When the toothbrush head 120 is attached to the toothbrush handle 110, the first end 111 of the toothbrush handle 110 and the first end 121 of the toothbrush head 120 abut one another.

In some embodiments, the longitudinal axis 123 of the toothbrush head 120 can be substantially parallel to, and can even coincide with, the longitudinal axis 113 of the toothbrush handle 110 when the toothbrush head 120 is attached to the toothbrush handle 110, FIG. 1. In other embodiments, the longitudinal axis 123 of the toothbrush head 120 and the longitudinal axis 113 of the toothbrush handle 110 may be not parallel to one another—and may instead form an acute angle therebetween (not shown)—when the toothbrush head 120 is attached to the toothbrush handle 110.

The toothbrush head 120 has at least one cleaning element 125 disposed at the second end 122 of the toothbrush head 120. In FIGS. 1 and 2, the head 120 has a plurality of tufts 125, each comprising a plurality of cleaning elements 126, such as, e.g., bristles, affixed to a tuft carrier 124 mounted for driven motion at the second 122 of the toothbrush head 120. During brushing, the tuft carrier 124 moves in a desired pattern of movement, e.g., in a pattern including rotational oscillation, a pattern including linear oscillation, a pattern including pivoting oscillation, or any combination thereof, based on the design of the toothbrush 10. Toothbrushes structured for various vibratory (non-rotational) movements are also known in the art. A power switch, such as, e.g., an ON/OF push button 160, can be conveniently located on a front surface 114 of the toothbrush handle 110.

As is known in the art, the toothbrush 10 may have a number of modes of operation, each characterized by a frequency and/or an amplitude with which its functional element, e.g., at least one cleaning element 125, moves (e.g., vibrates, oscillates, rotates). Each mode could be designed to perform a certain function, e.g., daily-clean brushing, soft brushing, intense brushing, tongue-cleaning, and the like. The frequency of the movement of the at least one cleaning element 125 could be, e.g., in the range of from about 50 Hz to about 300 Hz.

FIG. 2 shows a cross-sectional view of an embodiment of the toothbrush 10, in which the handle 120 houses inside a source of electric energy, such as, e.g., an electric battery 130, and an electric motor, such as, e.g., a direct-current (DC) motor 140 electrically connected to the battery 130. A motion transmitter 150, disposed in both the toothbrush handle 110 and the toothbrush head 120 and comprising an output shaft 151, converts and transmits the motor's continuous rotational movement to a brushing movement of the tuft support 124 and the cleaning elements 125. A controller, such, e.g., as a microcontroller 170 is in operative communication with the motor 140.

The microcontroller 170 may include a processor such as, e.g., one or more microprocessors, controllers, field programmable gate arrays (FPGAs) and application specific integrated circuits (ASICs), and/or any suitable type of processor. The microcontroller 170 may also include a memory (e.g., volatile memory, non-volatile memory) that stores machine-readable instructions corresponding to, e.g., the operations described with respect to the pressure-control system, including implementing the functionality described with respect to the stabilization phase and the overpressure-detection control loop.

As is previously described, the brushing movement may be chosen based on a particular design of the oral-care implement, including the design of the motion transmitter 150. In an exemplary embodiment of FIG. 2, illustrating the electric toothbrush 10, the motion transmitter 150 comprises a mechanism including, e.g., bevel (or miter) gears 152, providing oscillatory rotational movement of the tufts 125 comprising cleaning elements 126. However, other mechanisms and arrangements known in the art can be used to cause the desired movement of the implement's functional element 124. Likewise, electric known motors other than DC motors can be used to power the brush 10.

Figure 3:
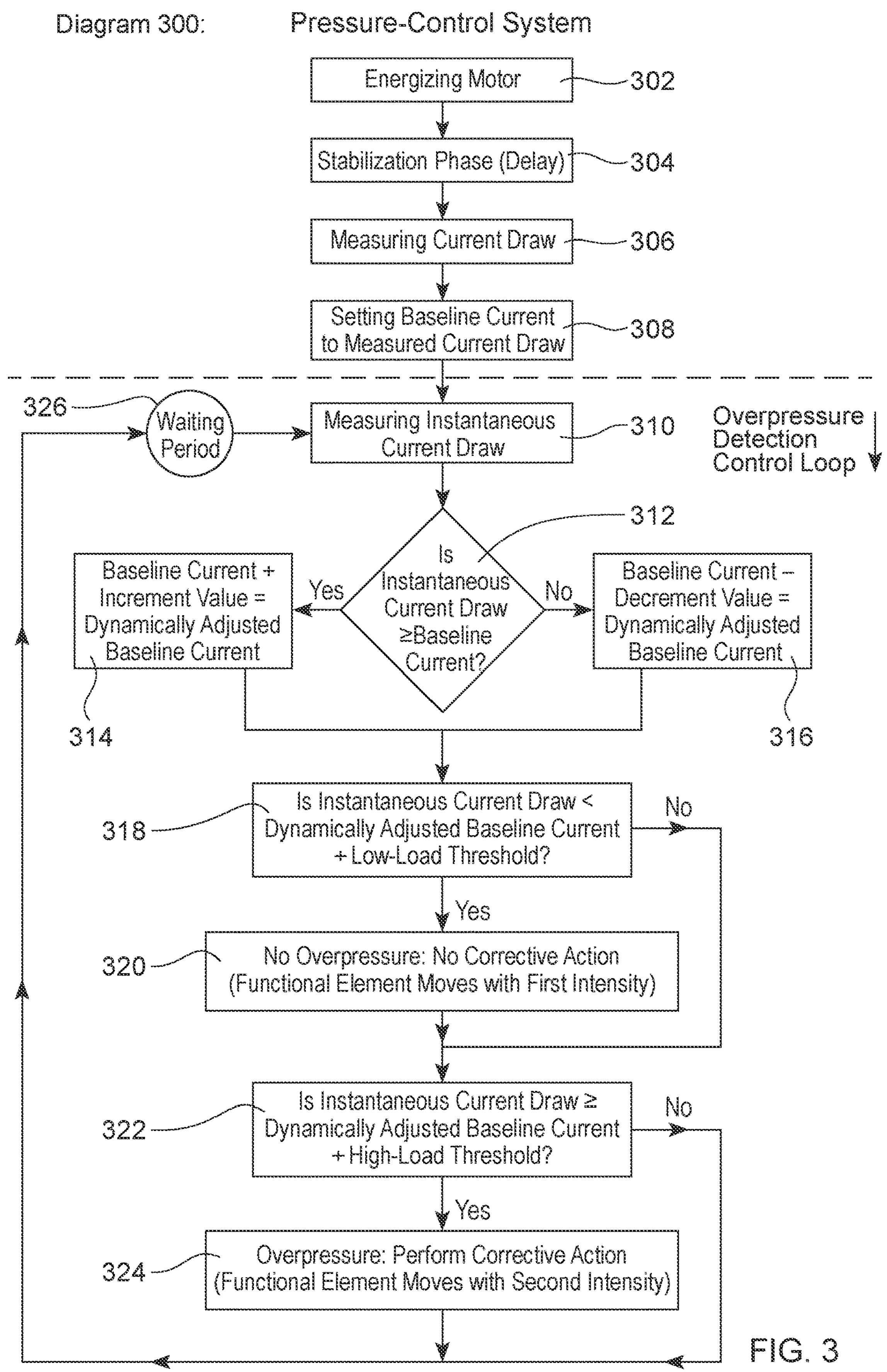
FIG. 3 is a flowchart of an algorithm implemented in an embodiment of a pressure-control system utilized in the oral-care implement.

As is shown in the diagram 300 of FIG. 3, an embodiment of the pressure-control system operates according to an algorithm that begins with the motor 140 being initially energized (FIG. 3, at 310). The microcontroller 170 first detects that the motor 140 is energized, e.g., by a user activating an ON/OFF switch (such as, e.g., a push button) 160. In an example embodiment illustrated in FIG. 3, the microcontroller 170 is configured to implement a stabilization phase or step (at 304), immediately following the detection that the motor 140 has been energized. During the stabilization phase, no measurements of the current draw to set the baseline current are taken, for at least the reasons explained below.

Most users of electric toothbrushes typically prefer to enable the toothbrush when the functional element 124 with the cleaning elements 126 (having toothpaste deposited thereon) are already in the user's mouth. Doing so avoids undesirable splattering water and toothpaste about—which would almost certainly occur when the brush is turned on and the functional element, having toothpaste deposited thereon, begins moving outside of the user's mouth. A user may start brushing while applying low pressure and gradually increasing pressure to a regular (habitual) brushing pressure in the process of brushing. Or the user may start brushing while applying the regular brushing pressure from the very beginning of brushing. These types brushing behaviors are difficult to specify and define with certainty.

At the same time, initially after the motor 140 is switched on, the initial current draw could be relatively high. The mechanical system, as well as the electronics, may need a brief period of time to warm up and acquire a stable condition. Thus, to avoid an incorrect indication of an excessive pressure based on the relatively high initial current draw, it could be advantageous to delay taking measurements for a duration of a stabilization phase. Therefore, the microcontroller 170 can be configured so that during the stabilization phase, the microcontroller does not measure the current draw to set the baseline current. The stabilization phase may last from about 500 milliseconds to about 5000 milliseconds, more specifically from about 1000 millisecond to about 3000 milliseconds. In one example embodiment, the duration of the stabilization phase is about 2000 milliseconds.

Thus, the stabilization phase is intended to let the motor 140 reach its full voltage and to allow a user sufficient time to bring the toothbrush 10 to the user's mouth, position the toothbrush cleaning elements 126 against the teeth, and start applying pressure to the cleaning elements 126. This would avoid setting the baseline current under a no-load condition. As is previously explained, measuring the motor current under a no-load (or "unloaded") condition would be unreliable for the purposes of calculating the overpressure threshold. Oppositely, measuring the motor current while the user is applying pressure to the toothbrush 10 inside the user's mouth, provides a realistic setting and delivers reliable basis for calculating the baseline current.

After the delay, taking place during the stabilization phase, has expired, the microcontroller 170 measures a current draw of the motor 140 (FIG. 3, at 306)—and sets a baseline current to the initial current measurement (at 308). Alternatively, the microcontroller 170 can be configured to set the baseline current to a predetermined value, e.g., a value in the range of from about 100 mA to about 600 mA.

After the baseline current has been set, the microcontroller 170 initializes the overpressure-detection control loop. If the user has already applied pressure to the toothbrush head 120 (most common, to avoid splashing the toothpaste), the initial current/baseline may be relatively high. As the user moves the brush 10 from tooth to tooth, the force on the brush head 120 could be periodically lower. Consequently, the measured current may periodically drop as well—and every time the current drops below the previous value, the baseline current is adjusted. Such adjustment of the baseline current to a lower value, as well as adjustment of the baseline current to a higher value, contributes to what is defined herein as "dynamically adjusted baseline current."

During the overpressure-detection control loop, the microcontroller 170 first measures an instantaneous current draw of the motor 140 (FIG. 3, at 310)—and then compares the measured instantaneous current draw to the baseline current. If the instantaneous current is equal to or higher than the baseline current (a high-load state of the motor) (at 312), then the microcontroller 170 adds an increment value to the baseline current (at 316). On the other hand, if the instantaneous current is lower than the baseline current (a low-load state of the motor), then the microcontroller 170 subtracts a decrement value from the baseline current (at 316). By adding an increment value to the baseline current or subtracting a decrement value from the baseline current, the microcontroller 170 generates the dynamically adjusted baseline current that would be used by the microcontroller 170 to detect an occurrence of overpressure (or its absence).

As is previously explained, the decrement value can generally be set to be greater than the increment value because the decrease of the baseline current has to happen faster than the increase thereof, as the low-load condition is shorter than the high-load condition. The decrement value could be at least ten times, twenty times, and even thirty times greater than the increment value. In one example embodiment, the increment value can be 0.1 mA. In one example embodiment, the decrement value can be 2 mA.

Then, to determine whether a difference between the instantaneous current draw and the dynamically adjusted baseline current exceeds the overpressure threshold, the microcontroller adds the overpressure threshold to the dynamically adjusted baseline current—and compares the instantaneous current draw to a sum of the dynamically adjusted baseline current and the overpressure threshold (FIG. 3, at 318). If the instantaneous current draw is higher than the sum of the dynamically adjusted baseline current and the overpressure threshold, then the microcontroller 170 sets an overpressure-detect flag to indicate that the motor 140 is operating in an overpressure state—and causes the toothbrush 10 to perform a corrective action in response to the detected occurrence of overpressure (at 322, 324). In other words, the pressure-control system determines that the motor 140 is in an overpressure state by detecting that the instantaneous current exceeds the dynamically adjusted baseline current by at least the overpressure threshold. The corrective action can be selected from the group consisting of slowing the speed of the motor, generating a light signal, generating a haptic signal, generating a sound signal, and any combination thereof.

If the instantaneous current draw is lower than the sum of the dynamically adjusted baseline current and the overpressure threshold, then the overpressure is not detected—and the microcontroller (a) either takes no additional action and waits for the start of the next control loop or (b) cancels the corrective action (e.g., increases the speed of the motor 140 back to its original speed) in response to detecting that the occurrence of overpressure has been eliminated (at FIG. 3, 320).

Frequency of executing the overpressure-detection control loop can be set to be a single overpressure-detection control loop every 1-1000 milliseconds, more specifically a single overpressure-detection control loop every 5-100 milliseconds, and even more specifically a single overpressure-detection control loop every 10 milliseconds. Depending on the desired frequency and duration the overpressure-detection control loop, the microcontroller 170 may be configured to implement a waiting period (FIG. 3, at 326) between two consecutive overpressure-detection control loops.

The overpressure threshold comprises a high-load (relatively high) threshold and a low-load (relatively low) threshold. The high-load threshold is indicative of the high-load state of the motor 140, i.e., when the motor 140 is in an overpressure state. The high-load threshold can be in the range of from about 100 mA to about 500 mA, and more specifically in the range of from about 150 mA to about 300 mA, depending on the chosen mode of operation of the brush 10. In one example embodiment, the high-load threshold can be about 200 mA.

The low-load threshold is indicative of the low-load state of the motor, i.e., the state in which low load is applied to the motor 140 (e.g., when the motor 140 is no longer in an overpressure state). To detect whether the occurrence of overpressure has been eliminated, the microcontroller 170 can be configured to determine whether the difference between the instantaneous current draw and the dynamically adjusted baseline current is less than the low-load threshold indicative of the low-load state of the motor. The low-load threshold is lower than the high-load threshold. The low-load threshold can be from about 20% to about 90% of the high-load threshold. For example, the low-load threshold can be from about 50 mA to about 400 mA. In one example embodiment, the low-load threshold is about 50% lower than the high-load threshold.

In one embodiment, if the difference between the instantaneous current draw and the dynamically adjusted baseline current is less than the low-load threshold, then the microcontroller 170 configures the motor 140 to cause the at least one functional element (i.e., cleaning elements 126) to move with a first (low-load) intensity. Then, in an event of detected overpressure, the corrective action may comprise configuring the motor 140 to cause the at least one functional element 126 to move with a second (high-load) intensity different from the first intensity. The second intensity may be lower than the first intensity. For example, the first intensity may comprise a regular speed of the motor 140, while the second intensity may comprise speed of the motor 140 that is reduced relative to the regular speed. Naturally, the functional element 126 driven by the motor 140 having a reduced speed would move slower than when driven by the motor 140 having a regular/normal speed.

By increasing or decreasing the baseline current value (i.e., by generating the dynamically adjusted baseline current) at each control loop, the pressure-control system adapts the overpressure threshold over time in a manner that accounts for the changes in the current draw introduced by differences in brush head 120 and/or wear and tear—and without relying on measurement of a no-load current draw.

Moreover, as is previously explained, the pressure-control system dynamically adjusts the baseline current during each overpressure-detection control loop (FIG. 3, at 312, 314, 316) before the comparison to the overpressure threshold is done. Thus, even if the electric toothbrush 10 is enabled in a no-load state of the motor 140, the dynamically adjusted baseline current value used in the comparison is not the measured no-load current draw—but instead an altered version of the current that has been increased by the increment value or decreased by the decrement value based on the result of the comparison of the instantaneous current to the baseline current.

In one embodiment, the microcontroller 170 performs two comparisons to determine the existence or absence of overpressure: a low-load comparison to detect the presence of an overpressure state and a high-load comparison to detect that the overpressure state has been resolved. In the high-load comparison (FIG. 3, at 322), the microcontroller 170 compares the instantaneous current to the sum of the dynamically adjusted baseline current and the high-load threshold, indicative of the high-load state of the motor 140. If the instantaneous current exceeds the sum of the dynamically adjusted baseline current and the high-load threshold, then the microcontroller 170 sets an overpressure-indicator flag to indicate that the motor 140 is operating in an overpressure state and reduces the speed of the motor 140.

In other words, the pressure-control system determines that the motor 140 is in an overpressure state by detecting that the instantaneous current exceeds the dynamically adjusted baseline current by at least the high-load threshold value. Conversely, if the instantaneous current is lower than the sum of the dynamically adjusted baseline current and the high-load threshold, then the microcontroller 170 takes no additional action and waits for the start of the next overpressure-detection control loop.

In the low-load comparison (FIG. 3, at 318), the microcontroller 170 compares the instantaneous current to the sum of the dynamically adjusted baseline current and the low-load threshold. If the instantaneous current is lower than the sum of the dynamically adjusted baseline current and the low-load threshold, then the microcontroller 170 sets the overpressure indicator flag to false to indicate that the motor 140 is no longer operating in an overpressure state and sets the speed of the motor 140 back to its original speed. Conversely, if the instantaneous current is greater than or equal to the sum of the dynamically adjusted baseline current and the low-load threshold, then the microcontroller 170 takes no additional action and waits for the start of the next overpressure-detection control loop.

The dimensions and values disclosed herein are not to be understood as being strictly limited to the exact numerical values recited. Instead, each such dimension is intended to mean both the recited value and a functionally equivalent range surrounding that value, unless otherwise specified herein. For example, a dimension disclosed as "40 mm" is intended to mean "approximately 40 mm" or "about 40 mm." Also, terms of approximation, such as, e.g., "approximately" and "about," could be used to refer to numerical values that may, in practice, embody something slightly different from the recited strict values. As such, these terms may, in the context of this disclosure, denote the degree by which a quantitative value, measurement, or other related representation may slightly vary from the stated exact value without resulting in a change in the basic function of the subject matter at issue.

A disclosure of every document cited herein, including any cross-referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated herein by reference, the meaning or definition assigned to that term in this document shall govern.

While particular embodiments of the present invention have been illustrated and described, it would be obvious to those skilled in the art that various other changes and modifications can be made without departing from the spirit and the scope of the invention. For example, several figures provided herein to illustrate exemplary embodiments should not be construed as limiting the invention, which is recited in the claims herein. It is therefore intended to cover in the appended claims all such changes and modifications that are within the scope of this invention.

What is claimed is:

1. A method for controlling overpressure in an electric oral-care implement having a treatment head with at least one functional element driven by a motor, the method comprising the steps:

detecting a stimulus to energize the motor;

setting a baseline current; and repeatedly execute an overpressure-detection control loop comprising the steps:

measuring an instantaneous current draw of the motor;

adding an increment value to the baseline current or subtracting a decrement value from the baseline current, thereby generating a dynamically adjusted baseline current;

determining whether a difference between the instantaneous current draw and the dynamically adjusted baseline current exceeds a threshold by adding the threshold to the dynamically adjusted baseline current, thereby detecting an occurrence of overpressure; and performing a corrective action in response to the detected occurrence of overpressure.

2. The method of claim 1, wherein the step of setting the baseline current comprises measuring a current draw of the motor and setting the baseline current to the measured current draw.

3. The method of claim 1, wherein the step of setting the baseline current comprises setting the baseline current to a predetermined value.

4. The method of claim 3, wherein the predetermined value is from about 100 mA to about 600 mA.

5. The method of claim 1, wherein the step of adding an increment value to the baseline current or subtracting a decrement value from the baseline current comprises:

adding the increment value to the baseline current if the instantaneous current is equal to or higher than the baseline current, or subtracting the decrement value from the baseline current if the instantaneous current is lower than the baseline current.

6. The method of claim 1, wherein the step of determining whether a difference between the instantaneous current draw and the dynamically adjusted baseline current exceeds the threshold comprises comparing the instantaneous current draw to a sum of the dynamically adjusted baseline current and the threshold.

7. The method of claim 1, wherein the method includes a step of detecting whether the occurrence of overpressure has been eliminated.

8. The method of claim 1, wherein in the step of adding an increment value to the baseline current or subtracting a decrement value from the baseline current, the decrement value is greater than the increment value.

9. The method of claim 8, wherein the decrement value is at least ten times greater than the increment value.

10. The method of claim 9, wherein the decrement value is at least twenty times greater than the increment value.

11. The method of claim 1, wherein in the step of adding an increment value to the baseline current or subtracting a decrement value from the baseline current, the decrement value is from about 0.66 mA to about 6 mA.

12. The method of claim 11, wherein the decrement value is about 2 mA.

13. The method of claim 1, wherein in the step of adding an increment value to the baseline current or subtracting a decrement value from the baseline current, the increment value is from about 0.03 mA to about 0.6 mA.

14. The method of claim 13, wherein the increment value is about 0.1 mA.

15. The method of claim 1, wherein the method includes a stabilization step in response to the detection of the stimulus to energize the motor, wherein during the stabilization step the measuring of the current draw to set the baseline current is delayed.

16. The method of claim 15, wherein the stabilization step lasts from about 500 milliseconds to about 5000 milliseconds.

17. The method of claim 16, wherein the stabilization step lasts about 2000 milliseconds.

18. The method of claim 1, wherein the overpressure-detection control loop is repeatedly executed once every 1-500 milliseconds.

19. The method of claim 18, wherein the overpressure-detection control loop is repeatedly executed once every 5-20 milliseconds.

20. The method of claim 19, wherein the overpressure-detection control loop is repeatedly executed once every 10 milliseconds.

21. The method of claim 1, wherein in the step of performing a corrective action, the corrective action is selected from the group consisting of slowing a speed of the motor, generating a light signal, generating a haptic signal, generating a sound signal, and any combination thereof.

22. The method of claim 21, wherein the speed of the motor is increased back to its original speed in response to detecting that the occurrence of overpressure has been eliminated.

23. The method of claim 21, wherein the method includes a step of detecting whether the occurrence of overpressure has been eliminated, said step comprising determining that the difference between the instantaneous current draw and the dynamically adjusted baseline current is less than the low-load threshold.

24. The method of claim 23, comprising configuring the motor to cause the at least one functional element to move with a first intensity upon the determination that the difference between the instantaneous current draw and the dynamically adjusted baseline current is less than the low-load threshold.

25. The method of claim 24, wherein the corrective action comprises configuring the motor to cause the at least one functional element to move with a second intensity different from the first intensity.

26. The method of claim 1, wherein in the step of determining whether a difference between the instantaneous current draw and the dynamically adjusted baseline current exceeds a threshold, the threshold comprises a high-load threshold indicative of a high-load state of the motor, and a low-load threshold indicative of a low-load state of the motor.

27. The method of claim 26, wherein the high-load threshold is from about 100 mA to about 500 mA.

28. The method of claim 26, wherein the low-load threshold is from about 20% to about 90% of the high-load threshold.

* * * * *